United States Patent
Zhu et al.

(10) Patent No.: US 6,650,940 B1
(45) Date of Patent: Nov. 18, 2003

(54) ACCELEROMETER-BASED HEART SOUND DETECTION FOR AUTOCAPTURE

(75) Inventors: Qingsheng Zhu, Little Canada, MN (US); Julio C. Spinelli, Shoreview, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/496,832

(22) Filed: Feb. 2, 2000

(51) Int. Cl.[7] .............................................. A61N 1/365
(52) U.S. Cl. ......................................... 607/28; 600/528
(58) Field of Search ............................. 607/28, 19, 27; 600/528

(56) References Cited

U.S. PATENT DOCUMENTS

| 4,708,142 A | * | 11/1987 | DeCote, Jr. ................. 607/28 |
| 4,763,646 A | * | 8/1988 | Lekholm ..................... 607/14 |
| 5,549,652 A | | 8/1996 | McClure et al. .............. 607/28 |
| 5,702,427 A | * | 12/1997 | Ecker et al. ................. 607/28 |
| 5,792,195 A | * | 8/1998 | Carlson et al. .............. 607/17 |
| 6,044,299 A | * | 3/2000 | Nilsson ....................... 607/19 |

* cited by examiner

*Primary Examiner*—Kennedy Schaetzle
(74) *Attorney, Agent, or Firm*—Nikolai & Mersereau, P.A.; C. G. Mersereau (57) ABSTRACT

An implantable cardiac rhythm management device capable of automatically detecting intrinsic and evoked response of a patient's heart. The device operates in an automatic capture verification mode, wherein a global accelerometer signal is utilized to identify heart sounds ($S_1$ and $S_2$) of the patient's heart. The presence or absence of one or more of the heart sounds $S_1$ and $S_2$ in the accelerometer signal indicates whether a stimulation pulse evokes a response by the patient's heart. The device may automatically adjust the stimulation output in accordance with a step down stimulation protocol, wherein the presence of a predetermined heart sound indicates capture. Also, the device may suspend the automatic capture verification sequence if the patient's physical activity level exceeds a predetermined threshold.

32 Claims, 5 Drawing Sheets

ACCELEROMETER-BASED HEART SOUND DETECTION FOR AUTOCAPTURE

FIELD OF THE INVENTION

This invention relates generally to a device for stimulating cardiac tissue, and more particularly relates to an implantable cardiac rhythm management device capable of automatically detecting intrinsic and evoked response of a patient's heart. The device of the present invention may operate in an automatic capture verification mode, wherein an accelerometer signal is utilized to identify heart sounds ($S_1$ and $S_2$) of the patient's heart. The presence or absence of one or more of the heart sounds $S_1$ and $S_2$ in the accelerometer signal may indicate whether a stimulation pulse evokes a response by the patient's heart. Further, the rhythm management device may automatically adjust the stimulation output in accordance with a step down stimulation protocol, wherein the presence of a predetermined heart sound indicates capture. Also, the device of the present invention may suspend the automatic capture verification mode if the patient's physical activity level exceeds a predetermined threshold.

BACKGROUND OF THE INVENTION

Cardiac rhythm management devices have enjoyed widespread use and popularity over the years as a means for supplanting some or all of an abnormal heart's natural pacing functions. The various heart abnormalities remedied by these stimulation devices include total or partial heart block, arrhythmias, myocardial infarctions, congestive heart failure, congenital heart disorders, and various other rhythm disturbances within the heart. A cardiac rhythm management device generally includes a pulse generator that generates stimulation pulses to the heart. The pulse generator is electrically coupled to an electrode lead arrangement (unipolar or bipolar) positioned adjacent or within a preselected heart chamber for delivering stimulation pulses to the heart.

Regardless of the type of cardiac rhythm management device that is employed to restore the heart's natural rhythm, all operate to stimulate excitable heart tissue cells adjacent to the electrode of the lead. Myocardial response to stimulation or "capture" is a function of the positive and negative charges found in each myocardial cell within the heart. More specifically, the selective permeability of each myocardial cell works to retain potassium and exclude sodium such that, when the cell is at rest, the concentration of sodium ions outside of the cell membrane is significantly greater than the concentration of sodium ions inside the cell membrane, while the concentration of potassium ions outside the cell membrane is significantly less than the concentration of potassium ions inside the cell membrane.

The selective permeability of each myocardial cell also retains other negative particles within the cell membrane such that the inside of the cell membrane is negatively charged with respect to the outside when the cell is at rest. When a stimulus is applied to the cell membrane, the selective permeability of the cell membrane is disturbed and it can no longer block the inflow of sodium ions from outside the cell membrane. The inflow of sodium ions at the stimulation site causes the adjacent portions of the cell membrane to lose its selective permeability, thereby causing a chain reaction across the cell membrane until the cell interior is flooded with sodium ions. This process, referred to as depolarization, causes the myocardial cell to have a net positive charge due to the inflow of sodium ions. The electrical depolarization of the cell interior causes a mechanical contraction or shortening of the myofibril of the cell. The syncytial structure of the myocardium will cause the depolarization originating in any one cell to radiate through the entire mass of the heart muscle so that all cells are stimulated for effective pumping. Following heart contraction or systole, the selective permeability of the cell membrane returns and sodium is pumped out until the cell is re-polarized with a negative charge within the cell membrane. This causes the cell membrane to relax and return to the fully extended state, referred to as diastole.

In a normal heart, the sino-atrial (SA) node initiates the myocardial stimulation of the atrium. The SA node comprises a bundle of unique cells disposed within the roof of the right atrium. Each cell membrane of the SA node has a characteristic tendency to leak ions gradually over time such that the cell membrane periodically breaks down and allows an inflow of sodium ions, thereby causing the SA node cells to depolarize. The SA node cells are in communication with the surrounding atrial muscle cells such that the depolarization of the SA node cells causes the adjacent atrial muscle cells to depolarize. This results in atrial systole wherein the atria contract to empty blood into the ventricles.

The atrial depolarization from the SA node is detected by the atrioventricular (AV) node which, in turn, communicates the depolarization impulse into the ventricles via the Bundle of His and Purkinje fibers following a brief conduction delay. In this fashion, ventricular systole lags behind atrial systole such that the blood from the ventricles pumps through the body and lungs after being filled by the atria (the atrial and ventricular systole generally create the first heart sound $S_1$). Atrial and ventricular diastole follow wherein the myocardium re-polarizes and the heart muscle relaxes in preparation for the next cardiac cycle (the atrial and ventricular diastole generally create the second heart sound $S_2$). It is when this system fails or functions abnormally that a cardiac rhythm management device may be needed to deliver an electrical stimulation pulse for selectively depolarizing the myocardium of the heart so as to maintain proper heart rate and synchronization of the filling and contraction of the atrial and ventricular chambers of the heart.

The success of a stimulation pulse in depolarizing or "capturing" the selected chamber of the heart hinges on whether the output of the stimulation pulse as delivered to the myocardium exceeds a threshold value. This threshold value, referred to as the capture threshold, is related to the electrical stimulation output required to alter the permeability of the myocardial cells to thereby initiate cell depolarization. If the local electrical field associated with the stimulation pulse does not exceed the capture threshold, then the permeability of the myocardial cells will not be altered enough and depolarization will not result. If, on the other hand, the local electrical field associated with the stimulation pulse exceeds the capture threshold, then the permeability of the myocardial cells will be altered sufficiently such that depolarization will result.

The ability of a rhythm management device to detect capture is desirable in that delivering stimulation pulses having energy far in excess of the patient's capture threshold is wasteful of the rhythm management device's limited power supply. In order to minimize current drain on the power supply, it is desirable to automatically adjust the device such that the amount of stimulation energy delivered to the myocardium is maintained at the lowest level that will reliably capture the heart. To accomplish this, a process known as capture verification must be performed wherein the rhythm management device monitors to determine whether an evoked depolarization occurs in the pre-selected heart chamber following the delivery of each stimulus pulse to the pre-selected chamber of the heart.

Changes in the capture threshold may be detected by monitoring the efficacy of stimulating pulses at a given energy level. If capture does not occur at a particular stimulation energy level which previously was adequate to effect capture, then it can be surmised that the capture threshold has increased and that the stimulation energy should be increased. On the other hand, if capture occurs consistently at a particular stimulation energy level over a relatively large number of successive stimulation cycles, then it is possible that the capture threshold has decreased such that the stimulation energy is being delivered at level higher than necessary to effect capture.

Past rhythm management devices have used electrode lead arrangements to sense an electrocardiogram signal from the patient's heart and then utilize the sensed electrocardiogram signal during a capture verification mode, to determine if a stimulation pulse evokes a response by the heart. Fusion beats, artifacts, and/or noise may affect the electrocardiogram signal and may result in an erroneous conclusion concerning capture. As a result, the capture threshold may be identified at a lower amount than the actual threshold.

McClure et al. in U.S. Pat. No. 5,549,652 describes a system for automatic capture verification, wherein the system described by McClure et al. requires an implantable lead positioned within the heart and containing a cardiac wall motion sensor. In some instances it may desirable to replace the rhythm management device without replacing the implanted lead. Hence, unless the implanted lead contains a cardiac wall motion sensor, the system for autocapture verification described by McClure et al. is apparently ineffective as a replacement device, thereby limiting the versatility and applicability of the McClure et al. system. Thus, there is a need for a capture verification system that is unaffected by fusion beats, artifact and noise and which is not limited to a lead having specialized additional components. The present invention meets these and other needs that will become apparent from a review of the description of the present invention.

SUMMARY OF THE INVENTION

The present invention provides a cardiac rhythm management device capable of verifying that a stimulation output evokes a response in a selected region of the heart. The device of the present invention may function in a preset stimulation and/or autocapture mode, wherein a stimulation rate and timing interval of the device is preset. The rhythm management device generally includes a pulse generator, an accelerometer, and a controller. The pulse generator is electrically coupled to the controller and generates a stimulation pulse for delivery to at least one of an atrium and a ventricle of a heart. The accelerometer is also electrically coupled to the controller and transmits a signal to the controller, wherein the transmitted signal from the accelerometer is associated with accelerations of the heart and in particular is associated with fluid and myocardial accelerations of the heart. The controller includes means for identifying heart sounds or pulse pressure from the signal of the accelerometer over corresponding cardiac cycles and also includes means for determining whether the identified heart sound is associated with delivery of the stimulation pulse to the heart.

In the preferred embodiment, the accelerometer is electrically coupled to a band pass filter having a range of between 20–70 Hertz for filtering the'signal associated with fluid and myocardial accelerations of the heart. The controller may include a program or dedicated device of known suitable construction that defines a timing interval or window having a predefined duration, wherein the signal from the accelerometer is analyzed for the presence of increased pulse pressure or heart sounds during the timing interval or window. In an embodiment of the present invention, the controller determines a maximum output of the accelerometer signal relative to time during the window for at least one cardiac cycle. The midpoint or center of the timing interval or window is then set equal to the time at which the maximum output of the first cardiac cycle occurs.

The controller may utilize the signals from the accelerometer to determine whether capture occurs during a step down stimulation protocol. Various methods may be incorporated by the controller to identify heart sounds during the step down stimulation protocol. For example, during the timing interval or window the accelerometer signal may be rectified and low pass filtered and then compared for a substantial increase in amplitude. Likewise, the accelerometer signal may be signal processed to eliminate those portions of the signal associated with compressions, blood fluid motions and/or global cardiac wall accelerations and decelerations caused from cardiac activity along with motion artifacts and respiratory events. Alternatively, the signal energy may be analyzed or a cross correlation may be made between the signal output for known captured beats and the test stimulation beats.

In another embodiment of the invention, the controller determines a patient activity level and terminates the determination whether the identified heart sound is associated with delivery of the stimulation pulse to the heart when the patient activity level exceeds a predetermined amount. The controller determines from the accelerometer signal the patient activity level.

In use, the device determines whether a stimulation output is sufficient to evoke a response in a patient's heart. An accelerometer is preferably positioned within the can or housing of the rhythm management device in order to obtain a globalized signal of the heart accelerations. Once a stimulation pulse is delivered having a predetermined output to a patient's heart, the accelerometer signal is received and analyzed by the controller of the rhythm management device. The accelerometer signal includes variations in the signal associated with fluid and myocardial accelerations of the heart. The heart sounds $S_1$ and/or $S_2$ are identified for each cardiac cycle corresponding with the stimulation pulse. Once the accelerometer signal is analyzed, then the controller determines whether the identified heart sounds are associated with delivery of the stimulation pulse to the heart. In this manner capture of the heart may be verified. The advantages of the present invention will become readily apparent to those skilled in the art from a review of the following detailed description of the preferred embodiment especially when considered in conjunction with the claims and accompanying drawings in which like numerals in the several views refer to corresponding parts.

DETAILED DESCRIPTION

Figure 1:
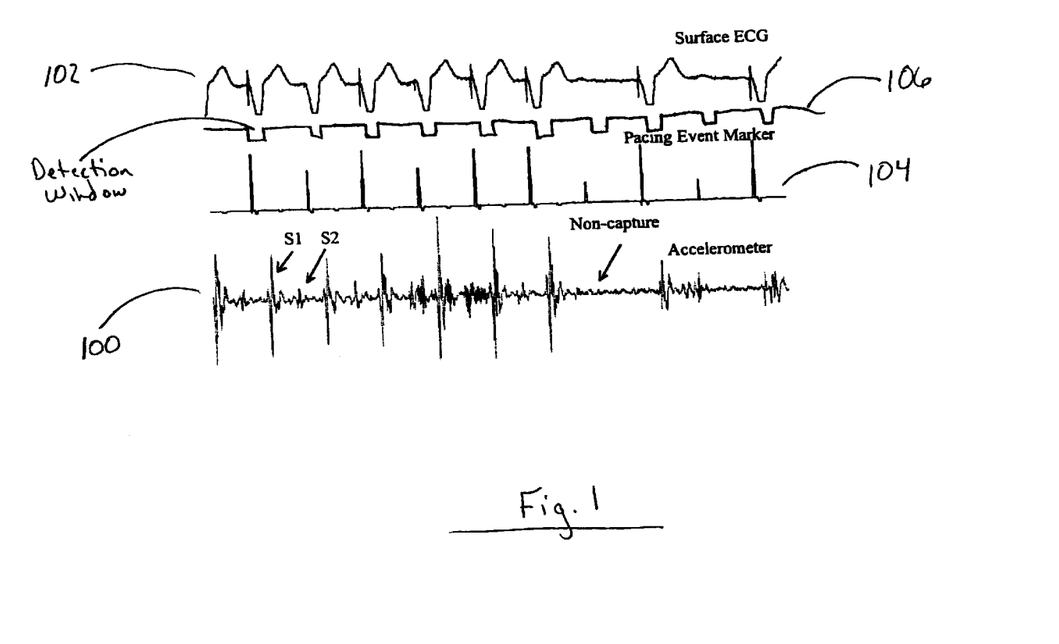
FIG. 1 is a graph of a surface electrocardiogram signal, a detection baseline, a pacing event marker, and an accelerometer signal each observed over the same cardiac cycles and aligned with respect to time for comparison.

The present invention represents broadly applicable improvements to cardiac rhythm management devices. The embodiments detailed herein are intended to be taken as representative or exemplary of those in which the improvements of the invention may be incorporated and are not intended to be limiting. Referring first to FIG. 1, there is shown an accelerometer signal 100, and surface electrocardiogram signal 102 sensed over time during a step down stimulation threshold protocol. The corresponding pacing event marker 104 and detection window 106 are also shown relative to the timing of the sensed events. As described below in greater detail, the first and second heart sounds $S_1$ and $S_2$ respectively are derived from the sensed accelerometer signal, wherein the presence or absence of $S_1$ and/or $S_2$ indicates whether a stimulation or paced event results in an evoked response or capture. Likewise, amplitude detection, signal energy comparison or cross correlation may be utilized to detect heart sounds occurring within the detection window 106 of the accelerometer signal 100.

Heart sound $S_1$ is preferably used for capture verification, however those skilled in the art will appreciate that heart sound $S_2$ may be used alone or in combination with an identification of heart sound $S_1$ to indicate capture. A predetermined time after the stimulus is delivered, the accelerometer signal 100 is analyzed by a controller for a predetermined duration (the "detection window" 106) for the occurrence of the pre-selected heart sound. If the heart sound is detected, capture is presumed. Without limitation, the accelerometer signal may be band-pass filtered having a band-pass of 20–70 Hertz to isolate portions of the signal unrelated to the heart sounds. Further, the detection window 106 may be utilized such that only a portion of the accelerometer signal is used to verify capture. In the preferred embodiment, the detection window is automatically initialized, wherein a first detected maximum output is used as the center (in time) of the detection window. The duration of the detection window is preferably between 100–300 milliseconds with a sample window of 10 milliseconds.

The accelerometer signal may also be utilized to identify when a patient's physical activity exceeds a predetermined amount. If the physical activity exceeds the predetermined amount, then automatic capture verification is suspended for a predetermined amount of time. For example, without limitation, the capture verification sequence may be suspended for 10 cardiac cycles, when the patient's physical activity detected by the accelerometer exceeds on average 50 mG over a period of time (one minute being preferred). In this manner, erroneous determination of capture due to patient physical activity is avoided.

Figure 2:
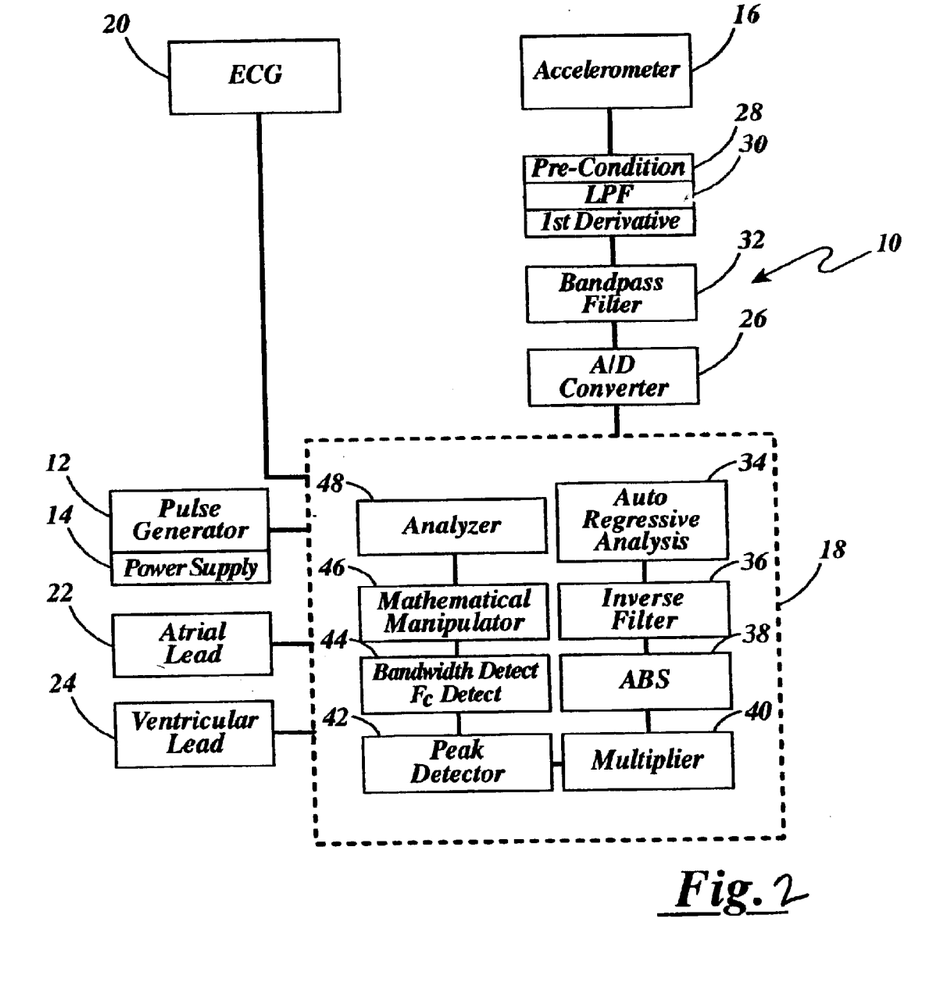
FIG. 2 is a block diagram of a portion of the electrical components of a cardiac stimulator of the present invention coupled to an atrial lead and a ventricular lead.

FIG. 2 shows in block diagram the preferred embodiment of the rhythm management device or cardiac stimulator 10 of the present invention. The cardiac stimulator 10 includes a pulse generator 12 having a power supply 14, an accelerometer 16, a microprocessor based controller (represented by a dotted line) 18, and an electrocardiogram (ECG) 20. The ECG 20 may be a surface or internal electrogram of known suitable construction, for identifying the timing of each cardiac cycle. Those skilled in the art will appreciate that the timing of the cardiac cycle may be determined with the use of other devices known suitable construction. A portion of the electrical components of the controller is shown enclosed by the dotted line 18. Atrial and ventricular leads 22 and 24 are shown coupled to the controller 18.

The controller controls the cardiac stimulating pulses delivered by pulse generator 12 to one or both of the leads 22 and 24, depending upon the pacing mode selected. Further, the controller establishes the optimal timing interval between stimulations of pre-selected chambers of the heart. The controller may be in any of several forms including a dedicated state device or a microprocessor with code, and may include both RAM (random access memory), and ROM (read only memory) for storing programs, data, and operands used in carrying out the computations by the controller which allows generally: the processing of signals from the electrogram and accelerometer 16, storing various information derived from the processing, and changing the preset constants of the program.

The accelerometer 16 is positioned within the casing of the cardiac stimulator or pacer and is coupled to the controller through an analog/digital converter 26 and filters further described below. The accelerometer 16 provides a signal that is processed to provide a non-intrusive measure of pulse pressure during a cardiac cycle. The casing of the cardiac pacer 10 is implanted in a surgically made pocket, typically in either the left or right shoulder region of the patient. By positioning the accelerometer 16 in the casing (not shown) of the cardiac pacer 10, the accelerometer 16 generates a global signal associated with various atrial and ventricular events. A globalized signal is preferred over a localized signal (a signal transmitted from an accelerometer in direct contact with an outer wall of the heart). The signal from the accelerometer 16 may also be used to evaluate levels of physical activity, thereby identifying periods in which physical activity is low.

An analog signal of the accelerometer 16 comprises events associated with heart sounds, compressions, blood fluid motions and/or global cardiac wall accelerations and decelerations caused from cardiac activity along with motion artifacts and respiratory events. Intermediate the accelerometer 16 and the controller 18, a preconditioning filter 28, low pass filter 30, band pass filter 32 and analog-to-digital (A/D) converter 26 are electrically coupled therebetween. The raw or analog signal transmitted from the accelerometer 16 passes through the preconditioning filter 28 and low pass filter 30 to produce a first derivative of the low pass filter signal.

The first derivative of the low pass filter signal then passes through a band pass filter and is digitized by an analog to digital (A-D) converter at 26. Preconditioning and filtering of the accelerometer signal enhances the pre-ejection accelerometer signature portion of the signal that is due to the on-set of ejection and further filters out other extraneous events. In this manner, a waveform is produced representative of heart sounds, eliminating non-essential frequencies utilizing the band pass filter 32 and eliminating the higher frequency components utilizing the low pass filter 30. The digital waveform is then transmitted from the A/D converter 26 to the controller 18, wherein the waveform first passes through an auto regressive analysis 34 using well-known Levinson or the Yule-Walker algorithms from autocorrelation lags of the accelerometer signal derived during the time of the main lobe of the energy signal. A discrete set of reflection coefficients representing the reference signal result. This coefficient set is fed to an inverse linear filter predictor 36.

The resulting coefficients then pass through an inverse linear predictor filter which produces an output indicative of the intensity or ongoing intensity energy level of the accelerometer signal as a function of time. The absolute value of this output is then subjected to a multiplier 40. The time of maximum absolute value of the spike corresponds to the time of minimum error with respect to the beginning of ejection. The preferred implementation of the inverse filter is that of an FIR lattice filter. This implementation results in a structure that is maximally numerically stable, since stable filters result in coefficient multiplication operations that are bounded in absolute value by 1.

The peak detector 42 is enabled and then a bandwidth and the center of frequency detectors identify values associated with the bandwidth and center of frequency ($F_c$). Once a value for the bandwidth and $F_c$ have been determined, then a mathematical manipulator 46 determines a value indicative of pulse pressure or heart sound from these values. The value indicative of pulse pressure or heart sound is repeatedly determined over a predetermined number of respiratory cycles and then a mean, maximum, or average value indicative of pressure may be determined. An analyzer 48 compares for example, the maximum value indicative of the pulse pressure for several preset pacing intervals during a step down pacing protocol and thereby determines the minimum stimulation output that results in an evoked response. The microprocessor based controller 18 then sets the stimulation output an amount above the determined minimum. Those skilled in the art will appreciate that the autocapture verification may be programmed to occur periodically or at a specific time each day so long as the patient's physical activity does not exceed a predetermined threshold.

Figure 3:
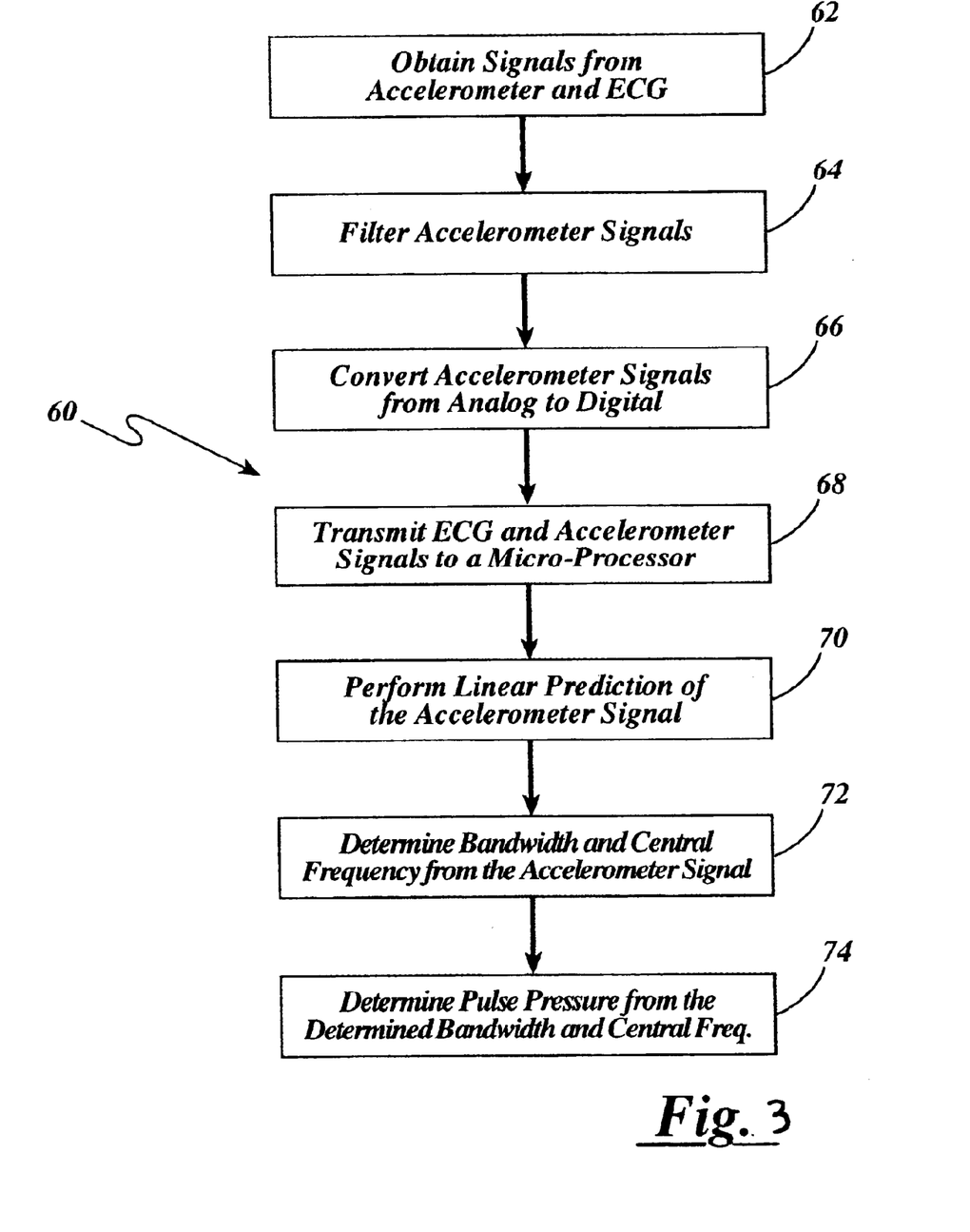
FIG. 3 is a flow diagram of the steps used by the controller to determine the pulse pressure from a signal transmitted by an accelerometer positioned within the casing of a cardiac stimulator.

In further explaining the invention, and especially the flow chart of FIG. 3, it is assumed that the timing interval of the cardiac stimulation device 10 is preset to correlate the pulse pressure with the atrial-ventricular (A-V) interval. It should be emphasized that the invention is not to be limited to use in a system where only the A-V delay interval is adjusted, and the results of the adjustment on pulse pressure noted. Those skilled in the art will recognize that the algorithm described equally applies to other timing intervals for any of a number of pacing modes. For example, the lower rate limit interval (R-R), the interval between right and left atrial stimulations ($A_R$-$A_L$ interval), the interval between right and left ventricular stimulations ($V_R$-$V_L$ interval), $A_R$-$V_R$ interval, $A_L$-$V_R$ interval, $A_R$-$V_{RL}$ I interval, $A_L$-$V_{RL}$ interval, $A_L$-$V_L$ interval etc. may be subjected to periodic changes with the effects on the pulse pressure being noted and stored.

The algorithm 60 shown in FIG. 3 is used to non-intrusively extract the hemodynamic pulse pressure from an accelerometer signal. Initially, signals from both the accelerometer 16 and ECG 20 are initiated to produce signals corresponding to the cardiac motion and cardiac cycles (see Block 62). The signal produced by the ECG is used to correlate a measured pulse pressure with the cardiac cycle. The accelerometer's signal is then transmitted through a series of filters as described above, to remove ancillary information contained in the accelerometer signal (see block 64). The filtered analog accelerometer signal is then converted to a digital signal (see block 66). The digital signal and ECG signal are transmitted to the microprocessor based controller 18 (see block 68) for processing and analysis. The microprocessor based controller 18 then performs a linear prediction from the digital signals resulting in $K_1$ and $K_2$ and thereafter determines the $F_B$ (bandwidth) and $F_C$ (central frequency) of the linear prediction (see blocks 70 and 72), where $F_C$ is determined from the following:

$$\theta_F = \frac{-K_1(1+K_2)}{\sqrt{K_2}}$$

$$f_c = \frac{[\cos^{-1}(\theta_F)]}{2\pi}$$

and, $$p = \sqrt{K_2}$$

and, $F_B$ is determined from the following equations:

$$\theta_B = \frac{[4p - (1 - p^2)]}{2p} \text{ and } f_B = \frac{[\cos^{-1}(\theta_B)]}{\pi}$$

and
The determined bandwidth and center frequency are added to obtain a value associated with the pulse pressure (see block 74). As previously recognized, the non-intrusively determined pulse pressure may be utilized to enhance cardiac performance. By means of example, immediately below is a description of one method of utilizing the calculated pulse pressure to enhance cardiac performance.

An ordered set of pre-set A-V interval values may be programmed into the memory of the microprocessor based controller 18 at the time of implant by the physician. This timing interval set would contain a range of A-V interval values over which the unit will automatically switch. Oftentimes, the sequence of the set may comprise alternation between a baseline without pacing (intrinsic) and a randomly selected A-V interval (having a value somewhat less than the intrinsic A-V interval). This alternation reduces hysteresis and other effects that a previous A-V interval value may have on the next A-V interval.

The microprocessor receives a digitized accelerometer signal from the accelerometer. A portion of this signal represents the level of physical activity of the patient. An initial test may be made to determine whether the physical activity is less than a predetermined amount X, which is indicative of a patient at rest. When the patient is resting, the accelerometer readings are less subject to noise and motion artifacts.

When the physical activity is less than the predetermined amount X, the A-V interval index m is then set to 1. The A-V interval is periodically changed, determining the value indicative of pulse pressure over several cardiac cycles for each A-V interval. The microprocessor 18 simultaneously analyzes the electrogram 20 signal to thereby correlate the determined value indicative of pulse pressure with the respiratory cycles determined from the ECG signal. The microprocessor based controller 18 then compares values indicative of pulse pressure for each iterated A-V interval to determine which A-V interval setting results in the greatest value indicative of pulse pressure. The A-V interval setting is then set by the microprocessor based controller 18 to the optimum A-V interval value. The A-V interval remains at this optimum setting until a predetermined time period Z has passed. The analysis is then repeated to determine a new optimum A-V interval.

Figure 4:
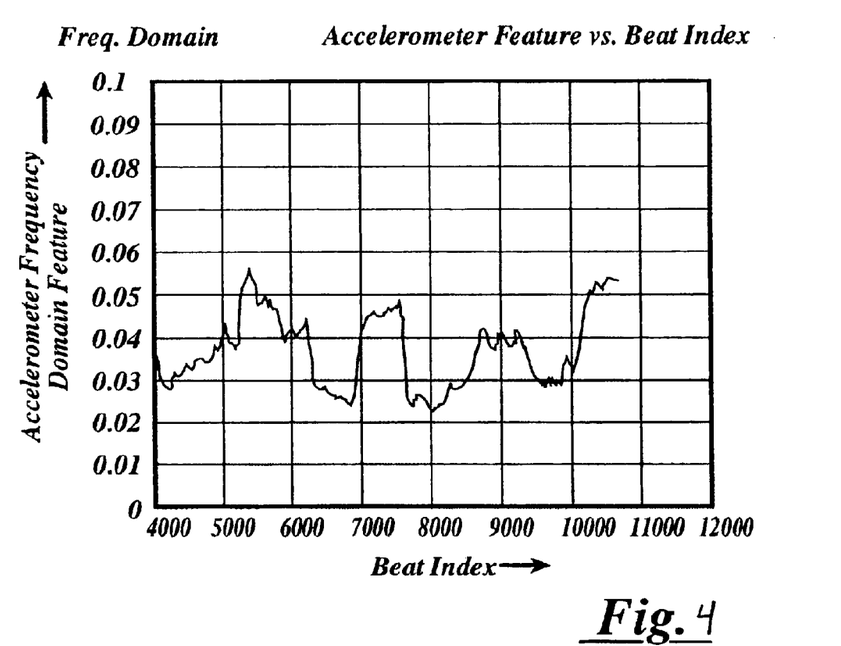
FIG. 4 is a graph of a frequency domain feature plotted over time (beat index) and extracted from an accelerometer signal of a non-intrusive accelerometer.
Figure 5:
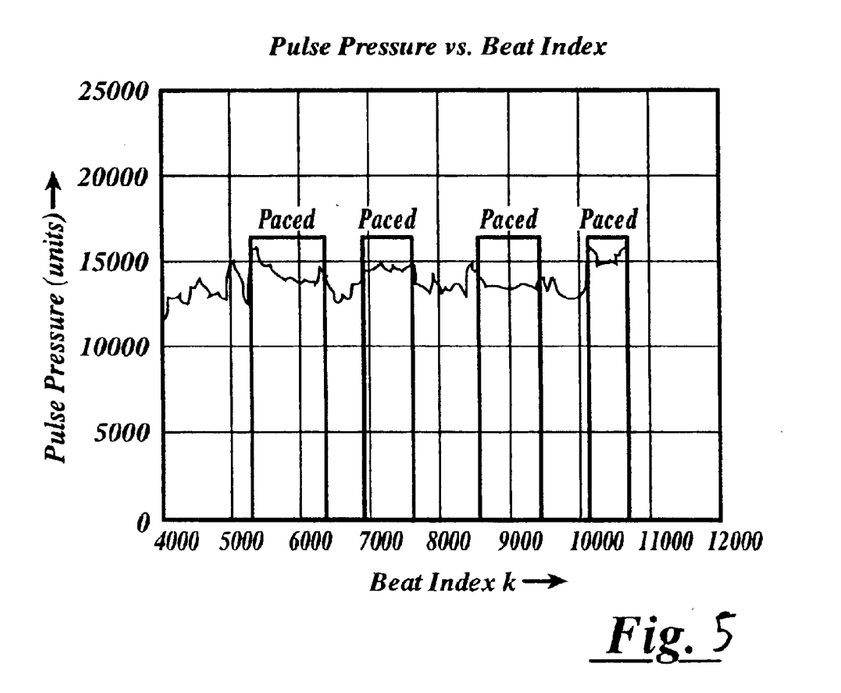
FIG. 5 is a graph of pulse pressure measured by an independent pulse pressure sensor plotted over the same beat index as FIG. 4 for comparison.
Figure 6:
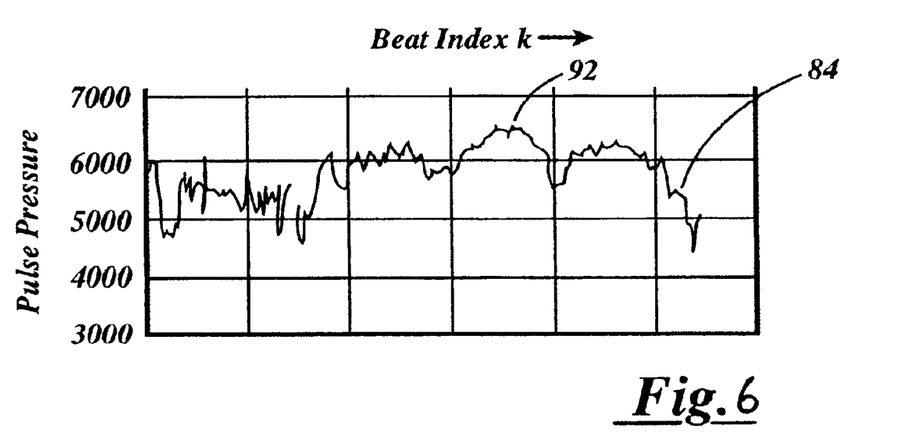
FIG. 6 is a graph of a pulse pressure measured by an independent pulse pressure sensor plotted over time (beat index)
Figure 7:
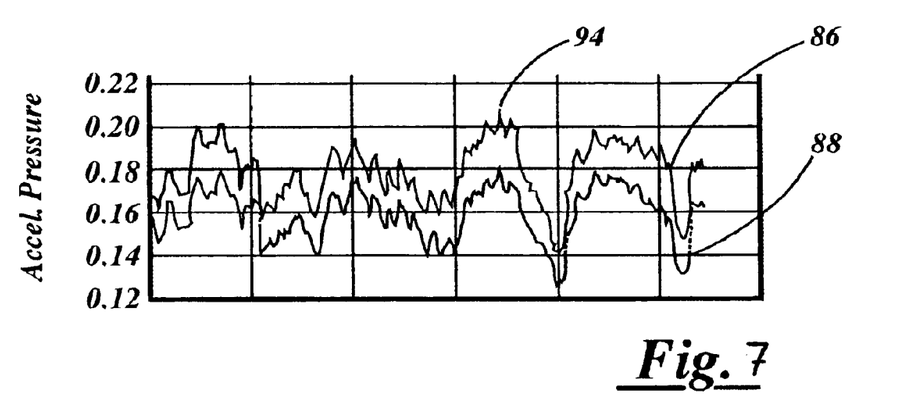
FIG. 7 is a graph of frequency domain features $K_1$ and $K_2$ extracted from an accelerometer signal over the same beat index as FIG. 6, and is shown for comparison.
Figure 8:
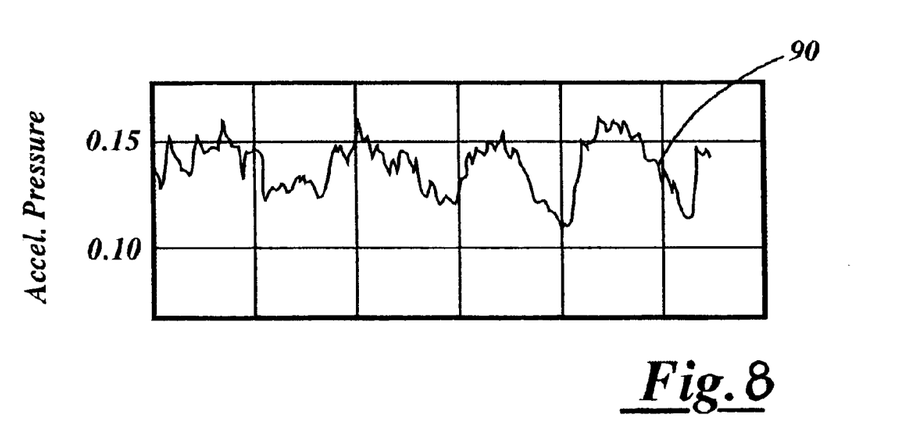
FIG. 8 is another graph of a frequency domain feature extracted from an accelerometer signal and plotted over time (beat index).

FIGS. 4–8 are various graphs illustrating graphically that a feature filtered from an accelerometer signal correlates with an independently measured pulse pressure or heart sound. By filtering the accelerometer signal, a waveform 80 of a specific event feature associated with pulse pressure is separated out from the accelerometer signal and is shown in FIG. 4 plotted over several cardiac cycles. The peaks in FIGS. 4–8 correspond with the ejection of blood fluid. FIG. 5 is a plot 82 of the pulse pressure values measured by a pulse pressure sensor. From a comparison of FIGS. 4 and 5 those skilled in the art will appreciate that the frequency domain feature derived from the accelerometer signal 80 correlates with the measured pulse pressure 82. Likewise, a comparison of FIG. 6 to FIGS. 7 and 8 illustrates that the peaks of a filtered accelerometer feature 84, 86, and 88 correspond with the peaks of a measured pulse pressure signal 90. Also, it can be seen that the maximum observed pulse pressure 92 in FIG. corresponds with the maximum accelerometer feature 94 in FIG. 7. Those skilled in the art will appreciate that for different pacing modes the maximum pulse pressure 100 may be used to identify an optimal timing interval 102.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A cardiac rhythm management device capable of functioning in a preset stimulation and/or autocapture mode having preset stimulation rates and timing intervals, said rhythm management device comprising:
    a pulse generator that generates a stimulation pulse for delivery to at least one of an atrium and a ventricle of a heart;
    an accelerometer that transmits a signal associated with accelerations of the heart;
    a controller electrically coupled to said pulse generator and said accelerometer, said controller identifying heart sounds from the signal of the accelerometer over corresponding cardiac cycles and further determining whether an identified heart sound is associated with delivery of the stimulation pulse to the heart;
    wherein said controller includes a detection window having a predefined duration;
    wherein said controller determines a maximum output of said signal of the accelerometer for at least one cardiac cycle; and
    wherein a center of the detection window is aligned with a determined maximum output of said signal of the accelerometer during a first cardiac cycle.

2. A cardiac rhythm management device according to claim 1, wherein said accelerometer is electrically coupled to a band pass filter having a range of between 20–70 Hertz for filtering the signal associated with accelerations of the heart.

3. A cardiac rhythm management device according to claim 1, wherein said means for determining whether an identified heart sound is associated with delivery of the stimulation pulse to the heart includes a step down stimulation protocol.

4. A cardiac rhythm management device according to claim 1, wherein the identified heart sound is associated with at least one of $S_1$ and $S_2$.

5. A cardiac rhythm management device according to claim 1, wherein the identified heart sound is associated with $S_1$.

6. A cardiac rhythm management device according to claim 1, wherein the identified heart sound is associated with $S_2$.

7. A cardiac rhythm management device capable of functioning in a preset stimulation and/or autocapture mode having preset stimulation rates and timing intervals, said rhythm management device comprising:
    a pulse generator that generates a stimulation pulse for delivery to at least one of an atrium and a ventricle of a heart;
    an accelerometer that transmits a signal associated with accelerations of the heart;
    a controller electrically coupled to said pulse generator and said accelerometer, said controller identifying heart sounds from the signal of the accelerometer over corresponding cardiac cycles and further determining whether an identified heart sound is associated with delivery of the stimulation pulse to the heart; and
    wherein said controller determines a patient activity level and terminates the determination as to whether the identified heart sound is associated with delivery of the stimulation pulse to the heart when the patient activity level exceeds a predetermined amount.

8. A cardiac rhythm management device according to claim 7, wherein the patient activity level is determined from the signal of the accelerometer.

9. A cardiac rhythm management device capable of functioning in a preset stimulation and/or autocapture mode having preset stimulation rates and timing intervals, said rhythm management device comprising:
    generating means for generating a stimulation pulse for delivery to at least one of an atrium and a ventricle of a heart;
    means for detecting and transmitting a signal associated with accelerations of the heart;
    control means electrically coupled to said generating means and means for detecting, said control means for identifying heart sounds from the signal of the means for detecting occurring during a predefined period and corresponding to a cardiac cycle, and wherein said control means determines whether an identified heart sound is associated with delivery of the stimulation pulse to the heart;
    wherein said control means determines a maximum output of the signal of the means for detecting for at least one cardiac cycle; and
    wherein a midpoint of the predefined period is set to correspond with a timing of detection of a determined maximum output of the signal of the means for detecting during a first cardiac cycle.

10. A cardiac rhythm management device according to claim 9, wherein said means for detecting is electrically coupled to a band pass filter having a range of between 20–70 Hertz for filtering the signal associated with fluid and myocardial accelerations of the heart.

11. A cardiac rhythm management device according to claim 9, wherein said control means includes a step down stimulation protocol.

12. A cardiac rhythm management device according to claim 9, wherein the identified heart sound is associated with at least one of $S_1$ and $S_2$.

13. A cardiac rhythm management device according to claim 9, wherein the identified heart sound is associated with $S_1$.

14. A cardiac rhythm management device according to claim 9, wherein the identified heart sound is associated with $S_2$.

15. A cardiac rhythm management device capable of functioning in a preset stimulation and/or autocapture mode having preset stimulation rates and timing intervals, said rhythm management device comprising:

generating means for generating a stimulation pulse for delivery to at least one of an atrium and a ventricle of a heart;

means for detecting and transmitting a signal associated with accelerations of the heart;

control means electrically coupled to said generating means and means for detecting, said control means for identifying heart sounds from the signal of the means for detecting occurring during a predefined period and corresponding to a cardiac cycle, and wherein said control means determines whether an identified heart sound is associated with delivery of the stimulation pulse to the heart; and wherein said control means determines a patient activity level and terminates the determination whether the identified heart sound is associated with delivery of the stimulation pulse to the heart when the patient activity level exceeds a predetermined amount.

16. A cardiac rhythm management device according to claim 15, wherein the patient activity level is determined from the signal of the means for detecting.

17. A method of determining whether a stimulation output is sufficient to evoke a response in a patient's heart, said method comprising the steps of:

positioning an accelerometer adjacent a patient's heart;

delivering a stimulation pulse having a predetermined output to a patient's heart;

obtaining from the accelerometer a signal associated with fluid and myocardial accelerations of the heart;

identifying heart sounds from the signal of the accelerometer over a cardiac cycle corresponding with the stimulation pulse;

determining whether the identified heart sounds are associated with delivery of the stimulation pulse to the heart; and determining a patient activity level and terminating the determination of whether the identified heart sound is associated with delivery of the stimulation pulse to the heart when the patient activity level exceeds a predetermined amount.

18. A method according to claim 17, wherein the patient activity level is determined from the signal of the accelerometer.

19. A method according to claim 17, further including electrically coupling a band pass filter to said accelerometer, said band pass filter having a range of between 20–70 Hertz for filtering the signal associated with fluid and myocardial accelerations of the heart.

20. A method according to claim 17, wherein the step of identifying heart sounds occurs during a detection window having a predefined duration.

21. A method according to claim 17, wherein the determination of determining whether the identified heart sounds are associated with delivery of the stimulation pulse to the heart includes a step down stimulation protocol.

22. A method according to claim 17, wherein the step of identifying heart sounds further includes identifying heart sounds associated with at least one of $S_1$ and $S_2$.

23. A method according to claim 17, wherein the step of identifying heart sounds further includes identifying a heart sound associated with $S_1$.

24. A method according to claim 17, wherein the step of identifying heart sounds further includes identifying a heart sound associated with $S_2$.

25. A cardiac rhythm management device capable of functioning in a preset stimulation and/or autocapture mode having preset stimulation rates and timing intervals, said rhythm management device comprising:

a pulse generator that generates a stimulation pulse for delivery to at least one of an atrium and a ventricle of a heart;

an accelerometer positioned near the heart, wherein said accelerometer transmits a global signal associated with fluid and myocardial accelerations of the heart; and a controller electrically coupled to said pulse generator and said accelerometer, said controller including a device for identifying heart sounds from the signal of the accelerometer over corresponding cardiac cycles and a device for determining whether an identified heart sound is associated with delivery of the stimulation pulse to the heart;

wherein said controller includes a detection window having a predefined duration;

wherein said controller determines a maximum output of the accelerometer signal for at least one cardiac cycle; and wherein a center of the detection window is aligned with a determined maximum output of the accelerometer signal during a first cardiac cycle.

26. A cardiac rhythm management device according to claim 25, wherein said accelerometer is electrically coupled to a band pass filter having a range of between 20–70 Hertz for filtering the signal associated with fluid and myocardial accelerations of the heart.

27. A cardiac rhythm management device according to claim 25, wherein said means for determining whether an identified heart sound is associated with delivery of the stimulation pulse to the heart includes a step down stimulation protocol.

28. A cardiac rhythm management device according to claim 25, wherein the identified heart sound is associated with at least one of $S_1$ and $S_2$.

29. A cardiac rhythm management device according to claim 25, wherein the identified heart sound is associated with $S_1$.

30. A cardiac rhythm management device according to claim 25, wherein the identified heart sound is associated with $S_2$.

31. A cardiac rhythm management device capable of functioning in a preset stimulation and/or autocapture mode having preset stimulation rates and timing intervals, said rhythm management device comprising:

a pulse generator that generates a stimulation pulse for delivery to at least one of an atrium and a ventricle of a heart;

an accelerometer positioned near the heart, wherein said accelerometer transmits a global signal associated with fluid and myocardial accelerations of the heart; and a controller electrically coupled to said pulse generator and said accelerometer, said controller including a device for identifying heart sounds from the signal of the accelerometer over corresponding cardiac cycles and a device for determining whether an identified heart sound is associated with delivery of the stimulation pulse to the heart; and wherein said controller determines a patient activity level and terminates the determination whether the identified heart sound is associated with delivery of the stimulation pulse to the heart when the patient activity level exceeds a predetermined amount.

32. A cardiac rhythm management device according to claim 31, wherein the patient activity level is determined from the signal of the accelerometer.

* * * * *